(12) United States Patent
Blomqvist et al.

(10) Patent No.: US 8,750,979 B2
(45) Date of Patent: Jun. 10, 2014

(54) METHOD AND IMPLANTABLE MEDICAL DEVICE (IMD) FOR MONITORING PERMEABILITY STATUS OF CELL MEMBRANES

(75) Inventors: Andreas Blomqvist, Spånga (SE); Anna-Karin Alm, Oskarsborg (SE); Jörgen Edvinsson, Sollentuna (SE); Kjell Norèn, Solna (SE); Christopher Graae, Järfälla (SE)

(73) Assignee: St. Jude Medical, AB, Jarfalla (SE)

( * ) Notice: Subject to any disclaimer, the term of this patent is extended or adjusted under 35 U.S.C. 154(b) by 472 days.

(21) Appl. No.: 12/865,169

(22) PCT Filed: Jan. 29, 2008

(86) PCT No.: PCT/SE2008/000079
§ 371 (c)(1),
(2), (4) Date: Jul. 29, 2010

(87) PCT Pub. No.: WO2009/096821
PCT Pub. Date: Aug. 6, 2009

(65) Prior Publication Data
US 2010/0331719 A1     Dec. 30, 2010

(51) Int. Cl.
*A61B 5/053*     (2006.01)
(52) U.S. Cl.
CPC ............... *A61B 5/053* (2013.01); *A61B 5/0538* (2013.01)
USPC ........................................................ 600/547
(58) Field of Classification Search
USPC ........................................................ 600/547
See application file for complete search history.

(56) References Cited

U.S. PATENT DOCUMENTS

| | | | | | |
|---|---|---|---|---|---|
| 4,537,203 | A | * | 8/1985 | Machida | 600/547 |
| 4,909,261 | A | * | 3/1990 | Rothenberg | 600/547 |
| 5,069,223 | A | * | 12/1991 | McRae | 600/547 |
| 5,280,429 | A | * | 1/1994 | Withers | 378/70 |
| 5,454,377 | A | * | 10/1995 | Dzwonczyk et al. | 600/547 |
| 5,746,214 | A | * | 5/1998 | Brown et al. | 600/547 |
| 5,807,270 | A | | 9/1998 | Williams | |
| 5,807,272 | A | * | 9/1998 | Kun et al. | 600/547 |
| 6,125,297 | A | * | 9/2000 | Siconolfi | 600/547 |
| 6,496,020 | B1 | * | 12/2002 | Davey et al. | 324/674 |
| 6,560,480 | B1 | * | 5/2003 | Nachaliel et al. | 600/547 |
| 6,681,131 | B2 | * | 1/2004 | Kandori et al. | 600/409 |
| 6,714,813 | B2 | | 3/2004 | Ishigooka et al. | |

(Continued)

OTHER PUBLICATIONS

"Gap Junctional Permeability Is Affected by Cell vol. Changes and Modulates Volume Regulation," Ngezahayo et al., FEBS, vol. 276, No. 1,2 (1990) pp. 6-8.

(Continued)

Primary Examiner — Sean Dougherty
Assistant Examiner — Michael C Stout (57) ABSTRACT

An implantable medical device comprises a signal generator for generating a current signal having a frequency in a frequency window slightly less than the β-dispersion frequency of a tissue and applying the signal over the tissue. A signal measurer measures the resulting voltage signal and an impedance parameter is calculated from the applied and measured signal by a parameter determiner. A status monitor monitors the permeability status of cell membranes in the tissue based on this impedance parameter.

24 Claims, 5 Drawing Sheets

(56) References Cited

U.S. PATENT DOCUMENTS

| | | | | |
|---|---|---|---|---|
| 6,962,587 | B2* | 11/2005 | Johnson et al. | 606/41 |
| 7,283,870 | B2* | 10/2007 | Kaiser et al. | 600/547 |
| 7,638,341 | B2* | 12/2009 | Rubinsky et al. | 436/149 |
| 7,818,054 | B2* | 10/2010 | Fukumoto et al. | 600/548 |
| 7,910,374 | B2* | 3/2011 | Rubinsky et al. | 436/149 |
| 8,101,421 | B2* | 1/2012 | Rubinsky et al. | 436/149 |
| 2002/0035339 | A1* | 3/2002 | Kavet et al. | 600/547 |
| 2002/0119191 | A1* | 8/2002 | Nishino et al. | 424/458 |
| 2003/0023186 | A1* | 1/2003 | Ueda et al. | 600/547 |
| 2003/0199782 | A1* | 10/2003 | Gozani et al. | 600/547 |
| 2004/0102712 | A1* | 5/2004 | Belalcazar et al. | 600/547 |
| 2004/0186392 | A1 | 9/2004 | Ward et al. | |
| 2005/0283091 | A1* | 12/2005 | Kink et al. | 600/547 |
| 2006/0085048 | A1* | 4/2006 | Cory et al. | 607/48 |
| 2006/0184060 | A1* | 8/2006 | Belalcazar et al. | 600/547 |
| 2006/0229527 | A1* | 10/2006 | Takehara | 600/547 |
| 2006/0235326 | A1* | 10/2006 | Dzwonczyk et al. | 600/547 |
| 2006/0241357 | A1* | 10/2006 | Chirife | 600/301 |
| 2006/0293609 | A1* | 12/2006 | Stahmann et al. | 600/547 |
| 2007/0156061 | A1* | 7/2007 | Hess | 600/547 |
| 2007/0162081 | A1* | 7/2007 | Yu et al. | 607/18 |
| 2007/0250127 | A1* | 10/2007 | Stylos et al. | 607/18 |
| 2007/0293783 | A1* | 12/2007 | Ginor et al. | 600/547 |
| 2008/0007275 | A1* | 1/2008 | Rubinsky et al. | 324/694 |
| 2008/0177194 | A1* | 7/2008 | Zhang et al. | 600/513 |
| 2008/0215108 | A1* | 9/2008 | Zhu et al. | 607/17 |
| 2008/0270051 | A1 | 10/2008 | Essex et al. | |
| 2008/319336 | A1* | 12/2008 | Ward et al. | 600/547 |
| 2010/0268109 | A1* | 10/2010 | Wang | 600/547 |

OTHER PUBLICATIONS

"Bioelectrical Impedance and Strength Measurements in Patients with Heart Failure: Comparison with Functional Class," Martinez et al., Nutrition, vol. 23 (2007) pp. 412-418.

"Tissue Ischemia Detection Using Impedance Spectroscopy," Kun et al., Proceedings of the $16^{th}$ Annual International Conference of the IEEE (1994), pp. 868-869.

Monitoring of Water Content and Water Distribution in Ischemic Hearts, Schaefer et al., Biochemistry, vol. 61 (2003), pp. 85-92.

"Red Cell Membrane Disorders," Gallagher, Hematology (2005) pp. 13-18.

"Altered Potassium Homeostasis in Crohn's Disease," Schober et al., Eur. J. Nucl. Med., vol. 8 (1983) pp. 245-249.

"Altered Membrane Proteins and Permeability Correlate with Cardiac Dysfunction in Cardiomyopathic Hamsters," Ikeda et al, Am. J. Physiol. Heart Circ. Physiol., vol. 278 (2000) pp. H1362-H1370.

"The Transmembranous Passes of K+ in Brain Cortex Under Radiation and Chemical Influences and Their Modification with Natural Adaptogen," Severinovskaia et al., Radiats Biol. Radioecol., vol. 47, No. 1 (2007) pp. 117-124.

"An Investigation to Show the Effect of Lung Fluid on Impedance Cardiac Output in the Anaesthetized Dog," Peng et al., British Journal of Anaesthesia, vol. 95, No. 4 (2005) pp. 458-464.

"A Simulation Study of the Electrical Model of a Biological Cell," Ellappan et al., Journal of Electrostatics, vol. 63, No. 3-4 (2005) pp. 297-307.

* cited by examiner

METHOD AND IMPLANTABLE MEDICAL DEVICE (IMD) FOR MONITORING PERMEABILITY STATUS OF CELL MEMBRANES

BACKGROUND OF THE INVENTION

1. Field of the Invention

The present invention generally relates to cell membrane permeability monitoring, and in particular to a device and method for detecting changes in cell membrane permeability.

2. Description of the Prior Art

Before an ischemic and potentially fatal or at least dangerous event occurs in a tissue, it is often preceded by anoxic conditions in cells. If the cells get too little oxygen, the cell metabolism fails and the transport in and out of potassium and sodium ions becomes disturbed and may even stop. The disturbance of the sodium/potassium transport and ion balance causes an increased osmotic value inside the cells as compared to the cell exterior. The increased relative osmotic value contributes to water passing through the semi-permeable cell membrane and the pressure inside the cell increases. The influx of water causes a swelling of cell diameter and a so called intracellular edema.

United States Patent Application Publication No. 2005/0283091 discloses the usage of bioimpedance for diagnosing and early detection of edema in a tissue. A cross-correlation procedure is employed for obtaining static and dynamic edema indices. The procedure involves generating and applying an excitation signal. A reference signal is also generated to be a normalized, time-delayed version of the excitation signal. A resulting response signal is detected and is cross-correlated to the reference signal by multiplying the two signals and then averaging to obtain a cross-correlation product. The edema indices can then be calculated from the cross-correlation product and the time delay.

A low frequency interval, 10-1000 Hz, is used for estimating the amount of extracellular liquid in a test tissue. A high frequency interval, 10 kHz-10 MHz is also employed for determining the total amount of liquid in a normalized volume of the tissue. The amount of intracellular liquid in the tissue can then be determined as a difference between these two estimated liquid amounts.

SUMMARY OF THE INVENTION

The prior art solution for following intracellular liquid volume changes, such as detecting intracellular edema, utilizes a complex processing involving determination and processing of signal cross-correlation products. In addition, the prior art solution must use at least two excitation/reference signals in fundamentally different frequency ranges, putting high demands to the signal generating and applying equipment.

The present invention overcomes these and other drawbacks of the prior art arrangements.

It is a general object of the present invention to provide a permeability status monitoring using impedance signals.

It is another object of the invention to provide an implantable medical device having permeability status monitoring capability.

These and other objects are met by the invention as defined by the accompanying patent claims.

Briefly, the present invention encompasses an implantable medical device, such as a pacemaker, defibrillator or cardioverter, containing a signal source arranged for generating a current/voltage signal having a selected frequency in a frequency window extending from the β-dispersion frequency of cells in a monitored tissue to about 90% of the β-dispersion frequency. The implantable medical device is connected to two electrodes employed for applying the generated current/voltage signal to the tissue. The same or different electrodes sense a resulting voltage/current signal from the tissue.

A parameter determiner is implemented in the medical device for calculating an impedance parameter based on the measured voltage/current signal and the applied current/voltage signal. This impedance parameter is employed by a status monitor for monitoring the permeability status of the cell membranes in the tissue and detecting a condition causing an increased permeability of the tissue cell membranes.

By monitoring the tissue impedance in a frequency window slightly less than the β-dispersion frequency of the tissue, a very simple data processing can be used by the implantable medical device for detecting permeability-changing conditions, such as intracellular edema due to ischemic events. At the particular measurement frequency, a permeability change give rise to a large change in the impedance signal that can easily be detected by the status monitor.

In an optional embodiment, also a second measurement frequency present within a frequency interval slightly above the β-dispersion frequency can be used according to the invention. In such a case, a difference between a first impedance parameter measured at a frequency in the first window and a second impedance parameter measured at a frequency in the second window will be significantly less for a tissue having abnormally high membrane permeability as compared to a healthy tissue.

The β-dispersion frequency of the monitored tissue can be determined through a frequency sweep procedure by determining impedance parameters at multiple successive test frequencies. The determined β-dispersion frequency is then employed for defining the first and optionally the second measurement frequency used in the permeability status monitoring.

The invention offers the following advantages:
- Can be used for early detection of ischemia and other medical conditions causing intracellular edema and a change in cell membrane permeability;
- Provides a simple signal processing for determining effective monitor parameter through careful selection of measurement frequency;
- No special sensors are required but traditional implantable medical device units can be used; and
- Saves the limited processing power and battery power of implantable medical devices.

Other advantages offered by the present invention will be appreciated upon reading of the below description of the embodiments of the invention.

DESCRIPTION OF THE PREFERRED EMBODIMENTS

Throughout the drawings, the same reference characters will be used for corresponding or similar elements.

The present invention generally relates to an implantable medical device and the usage thereof in monitoring permeability status and detecting permeability changes in the cell membranes of a tissue. The invention is based on the finding that impedance measurements, such as complex impedance measurements, can be an efficient tool for diagnosing and following such membrane status changes. In addition, by careful choice of the used frequency in the impedance measurements, a simple processing algorithm can be used and still allow an efficient permeability status monitoring.

Figures 1, 2:
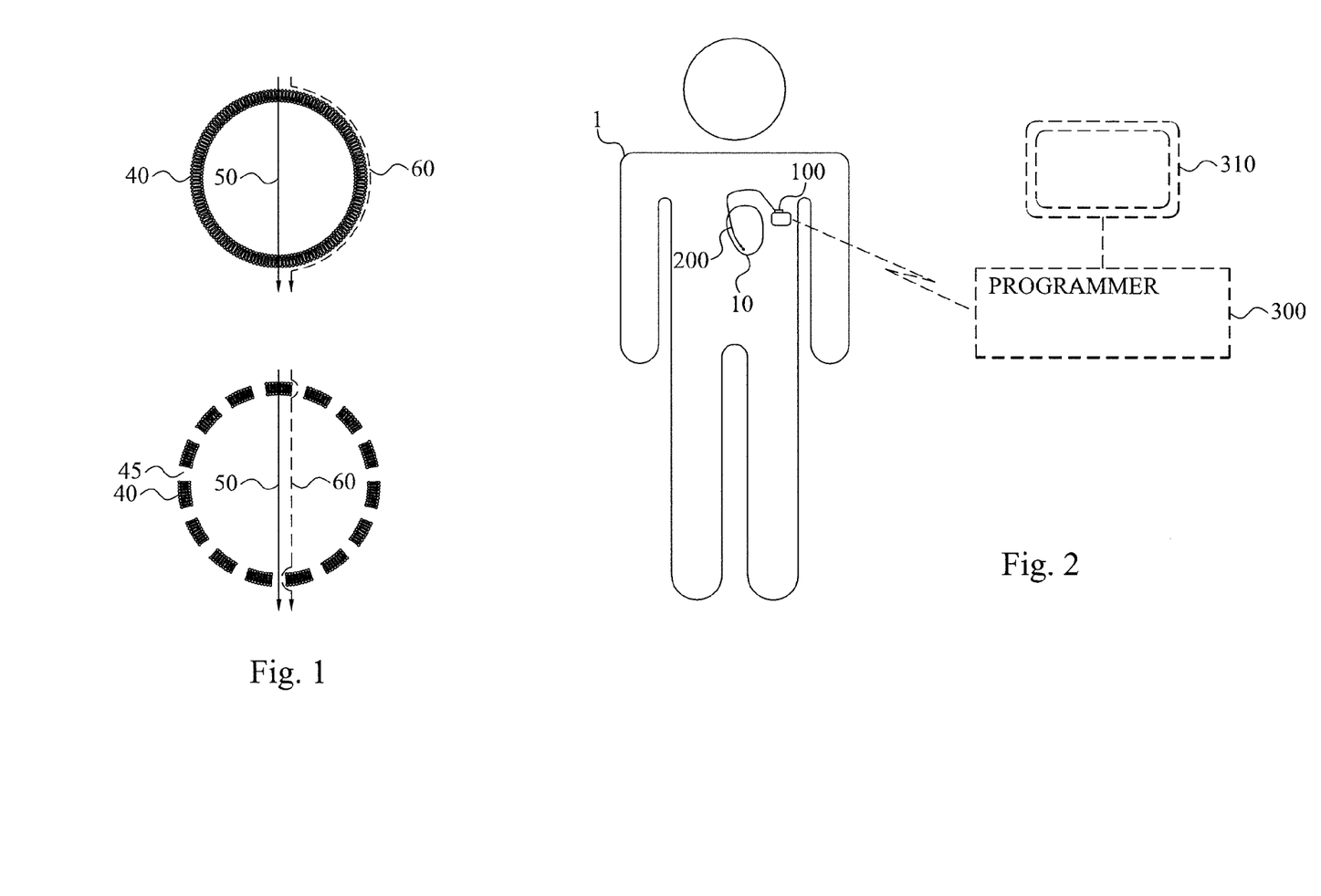
FIG. 1 is an illustration of current paths for a cell and an edemic cell.
FIG. 2 is a schematic overview of a patient having an implantable medical device according to the present invention and an external unit capable of conducting communication with the implantable medical device.

As is well known in the art, the cell can be described as an electrical circuit made up of capacitors and resistors. FIG. 1 schematically illustrates a cell with its double layered cell membrane 40 made of phospholipids. This cell membrane provides capacitance effects stopping all DC currents and most of the low-frequency currents 60. Thus, the current path of such DC and low-frequency currents 60 is found around and between the cells in a tissue. However, for high-frequency currents 50 the cell membrane 40 starts to act more like a short circuit allowing the high-frequency current 50 to pass through the membrane 40 (or the capacitor).

If the permeability of the membrane 40 changes, such as during an ischemic event with intracellular edema, the membrane 40 could be spread, due to the net inflow of water into the cell, over a larger area. Small gaps or channels 45 are formed in the cell membrane 40. This can be compared to a capacitor in which the two plates are approaching each other or small canals of more conducting material appear in the isolated material between the plates. As a consequence, not only the high-frequency current 50 but also the comparatively lower frequency current 60 can pass through the permeable membrane. The present invention is based on a technical application of these physical phenomena.

FIG. 2 is a schematic overview of a subject 1 equipped with an IMD 100 connected to the subject's heart 10. The IMD 100 is illustrated as a device that monitors and/or provides therapy to the heart 10 of the patient 1, such as a pacemaker, defibrillator or cardioverter. The IMD 100 is connectable to at least one medical lead 200, such as intracardiac, endocardiac or epicardial lead, connected to the heart 10. The medical lead 200 comprises electrodes in connection with its distal end connected or anchored in the heart 10. These electrodes are employed by the IMD 100 for generating the impedance signal utilized in the permeability monitoring of the invention.

In FIG. 2, the IMD 100 has been illustrated as an implantable medical device providing therapy and diagnosis to the heart 10 in the patient 1. However, the present invention is not limited thereto. In clear contrast the present invention can be used in connection with other forms of implantable devices having access to at least two implantable electrodes. Examples of such devices include implantable drug pumps, neurological stimulators, physical signal recorders, oxygen sensors, or the like.

The figure also illustrates an external programmer or clinician's workstation 300 that can communicate with the IMD 100. As is well known in the art, such a programmer 300 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the programmer 300 before display to a clinician on a connected display screen 310. In the light of the present invention, such diagnostic data can include membrane permeability data generated by the IMD 100 and/or other raw or partly processed (impedance) data relating to such permeability status monitoring.

Figures 3, 4:
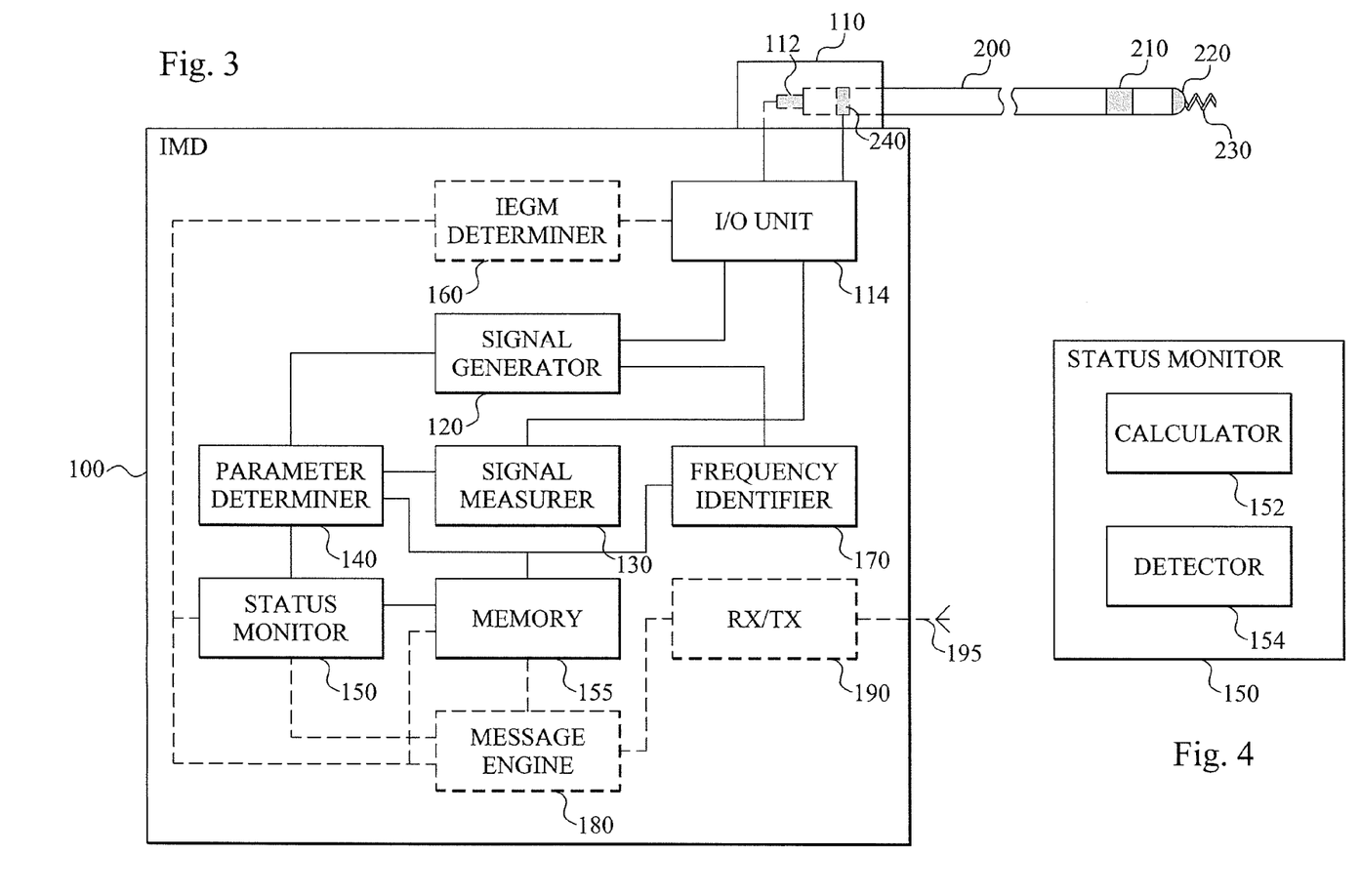
FIG. 3 is a schematic block diagram of an embodiment of an implantable medical device according to the present invention.
FIG. 4 is a schematic block diagram of the status monitor of FIG. 3.

FIG. 3 is a schematic block diagram of an embodiment of an implantable medical device 100 according to the present invention. In this embodiment, the IMD 100 is connected to at least two implantable electrodes 210, 220, 230 used for applying and sensing electric signals to and from a tissue, where permeability monitoring is desired. These electrodes 210, 220, 230 are preferably arranged on one or more implantable medical leads 200 connected to the IMD 100 through an electrode or lead connecting arrangement 110. As is well known in the art, such an implantable lead or catheter 200 has a proximal end connected to the IMD 100 through the connecting arrangement 110. This IMD-connecting end presents one or more electric terminals 240 that are in electric connection with the electrodes 210, 220, 230 present on the opposite distal lead end, where the electric connection is achieved by electric conductors running along the length of the lead body. The distal lead end with its electrodes 210, 220, 230 is then provided in connection with a tissue, preferably a heart tissue. For this purpose, the lead 200 can include a tissue anchoring element, such as a helical fixation element 230 illustrated in the figure, though other fixation elements, such as passive fixation elements, including fines, tines, etc., are also common. The fixation element 230 can indeed constitute one of the electrodes of the lead 200, while remaining electrodes 210, 220 can be ring electrodes (indifferent electrodes) 210, tip electrodes 220, defibrillation electrode, or the like.

The IMD 100 can be connected to a single medical lead 200, then preferably having at least two electrodes 210, 220, 230, such as ring electrode 210 and tip/helix electrode 220/230. Alternatively, the IMD 100 is connected to multiple, i.e. at least two, implantable leads having electrodes. In either case, the at least one lead 200 can be an intracardiac lead positioned in any of the chambers of the heart, such as right and/or left atrium and/or ventricle. Alternatively, the at least one lead 200 could be epicardially positioned relative the heart. Also a combination of intracardial and epicardial leads is contemplated by the present invention. Also non-cardiac leads can be used by the invention.

One of the electrodes utilized in the signal application and sensing of the present invention could be the can or case of the IMD 100. Thus, the present invention is not limited to lead-implemented electrodes 210, 220, 230.

The applying and sensing electrodes 210, 220, 230 of the invention can also be used by the IMD 100 for other purposes, such as for providing stimulating pulses, cardioversion pulses, defibrillation shocks and/or sensing electrical signal from the heart or other tissue.

The IMD 100 has a signal source 120, preferably a frequency tunable signal source. This signal source 120 is connected to two electrodes 210, 220, 230 through the electrode connecting arrangement 110 and an optional input and output (I/O) unit 114 providing an interface between the electrode terminals 112 of the connecting arrangement 110 and internal IMD units.

The signal source 120 is arranged for generating a current or voltage signal of selected frequency. The signal is an alternative current (voltage) signal having a particular frequency selected to be within a frequency window. This given frequency window extends from about the β-dispersion frequency of the cell membranes in the monitored tissue down to a frequency corresponding to about 90% of the β-dispersion frequency.

The permittivity of a cell material shows frequency-dependent dielectric relaxation, also known as dielectric dispersion. The dielectric spectrum of a biological cell suspension displays three such major dispersions, of which one is the β-dispersion. The β-dispersion, typically in the frequency range of 1 kHz to 1 GHz, is chiefly caused by interfacial polarization due to plasma membranes and is also called the Maxwell-Wagner effect in the art.

Briefly, the β-dispersion frequency of a cell is the frequency at which capacitance effect of the cell membrane becomes significant for an alternating current, allowing the current to pass through the cell. Thus, at a frequency lower than the β-dispersion frequency, the capacitance effects of the cell membrane stop the current from passing through the cell. Correspondingly, an alternating current of a frequency larger than the β-dispersion frequency can pass through the membrane. The β-dispersion can therefore be regarded as the frequency at which the transition from current-blocking to current-permitting effect occurs. The actual frequency of β-dispersion is to some extent cell dependent and may also depend on the particular tissue in which the cell is present and also the particular subject. For most animal cells, including human cells, the β-dispersion frequency is in the frequency range of from 1 kHz to 1 GHz. An average β-dispersion frequency could be about or around 100 kHz to 1 MHz.

The signal generator 120 of the invention, thus, generates a current or voltage signal of a frequency in a frequency interval at or slightly less than the β-dispersion of cell tissue of interest. This means that the applied current or resulting current will typically not be able to pass through the cell membrane or pass only partly therethrough.

The preferred frequency window extends from the β-dispersion frequency to about 90% of the β-dispersion frequency. In a more preferred embodiment, the window is present slightly below the β-dispersion frequency, i.e. from about 90% of to about 99% of the β-dispersion frequency. The signal generator 120 then selects an appropriate frequency within this interval to use for the alternating current or voltage signal to apply, using two connected electrodes 210, 220, 230, over a monitored tissue.

In this embodiment, the IMD 100 comprises a signal measurer 130 arranged connected to at least two electrodes 220, 220, 230 through the connecting arrangement 110 and the optional I/O unit 114. The measurer 130 is provided for measuring a resulting voltage or current signal sensed or captured by two electrodes 210, 220, 230 and originating from the tissue. This resulting voltage (current) signal is due to the applied current (voltage) signal from the signal source 120. In a preferred implementation, the signal measurer 130 generates a sensed (AC) voltage signal using its at least two connected electrodes 210, 220, 230.

The signal source 120 and the signal measurer 130 are connected to a parameter determiner 140 provided in the IMD 100 for determining an impedance parameter representative of the impedance of the tissue. The determiner 140 utilizes the measured or sensed voltage (current) signal from the measurer 130 together with information of the generated and applied current (voltage) signal from the signal source 120.

The parameter determiner 140 can utilize different filter combinations, such as bandpass filters, in order to obtain multiple different impedance signals based on the measured voltage signal and the applied current signal. In such a case, it is possible to achieve a set of impedance parameters at different frequencies of the applied bandwidth and individually process one or more of these signals. Alternatively, a "raw" or only partly filtered impedance signal can be used for the purpose of the present invention. The impedance parameter or signal determined by the parameter determiner 140 can be a complex impedance parameter, i.e. comprising a resistive and a reactive component or alternatively an impedance amplitude and phase angle. Alternatively, only the resistive or reactive component or the impedance amplitude is used as impedance parameter of the invention.

An impedance vector is generally employed for identifying the electrodes 210, 220, 230 used for signal application and signal sensing, respectively. As is known in the art, bipolar impedance vectors utilize the same two electrodes for both signal application and signal sensing. In tripolar impedance vectors, the current signal is applied to a tissue over two electrodes and is sensed over two electrodes, one of which but not the other was employed for the signal application. Finally, in quadropolar vectors, two dedicated signal applying electrodes are used and two dedicated different signal sensing electrodes.

Generally bipolar vectors typically give a more local representation of the tissue impedance in the close vicinity to the electrodes. Correspondingly, tripolar and quadropolar vectors could be advantageous when monitoring cell permeability changes in a tissue present between two medical leads to thereby mainly get an influence of the impedance signal from the intermediate tissue and not other surrounding tissues.

In order to increase the specificity in the measurements of the invention, different impedance vectors can be utilized for monitoring the permeability status. This can be useful if a particular impedance vector will be marred by large noise or captures other non-desired variations in the impedance signal. For this purpose, the signal source 120 can generate and apply a first current (voltage) signal to a tissue using a first set of two connected electrodes 210, 220, 230. The signal measurer 130 measures the resulting voltage (current) signal from the tissue with the same or different electrodes 210, 220, 230. The signal source 120 could then apply a second current signal, which could be a copy of the first signal, i.e. of the same frequency and amplitude, but then over a second set of two connected electrodes, of which at least one is different from the electrodes 210, 220, 230 of the first set. The signal measurer 130 once again measures the resulting voltage signal.

In an alternative approach, the signal source 120 applies two following current signals over the same electrode pair 210, 220, 230 but the signal measurer 130 senses the first resulting voltage utilizing a first set of two electrodes 210, 220, 230 and senses the second resulting voltage signal with a second set of two electrodes 212, 214.

The parameter determiner 140 can then calculate two "parallel" impedance parameters for the two different impedance vectors or determine the impedance parameter as an average of the two or more different vectors.

A status monitor 150 is arranged connected to the impedance determiner 140 for monitoring the permeability status of cell membranes in the tissue based on the determined impedance parameter.

In a preferred embodiment, the status monitor 150 is arranged for monitoring the permeability status based on a comparison of the determined impedance parameter and a reference impedance parameter. This reference parameter can be fetched from a connected memory 155 present in the IMD 100. The reference parameter is preferably a previously determined impedance parameter determined by the parameter determiner 140 at a previous time instance and then entered in the memory 155. As a consequence, the signal generator 120 could periodically or intermittently, such as once every minute, every 10 minutes, every 30 minutes, every hour, every second hour, every five hours, every 12 hours, once a day, once every second day or even more seldom, generate a current of voltage signal that is applied by the electrodes 210, 220, 230 over the interesting tissue. The signal measurer 130 measures the resulting voltage or current signal and the parameter determiner 140 uses information of the applied and measured signals for calculating the impedance parameter. This parameter is compared to a previously stored reference parameter and, preferably, if the there is no significant difference between the impedance parameter and the reference parameter, the determiner 140 updates the reference parameter based on the newly calculated parameter. As a consequence, the reference parameter can be an average, possibly weighted average, of multiple previously calculated impedance parameters originating from different measurement times.

Alternatively, the reference parameter can be a default parameter that is hard-coded in the IMD 100 or received by a receiver 190 from an external source. In such a case, the reference parameter is preferably an average reference impedance parameter as determined from multiple different measurements from multiple test subjects. However, the impedance parameter is highly dependant on the particular tissue to monitor, the impedance vector to use, the relative position of the electrodes, electrode-tissue connection status, etc. As a consequence, a reference parameter that is determined based on actual measurements in the current subject body utilizing the same electrodes and impedance vector(s) as are employed in the monitoring is preferred.

Figure 5:
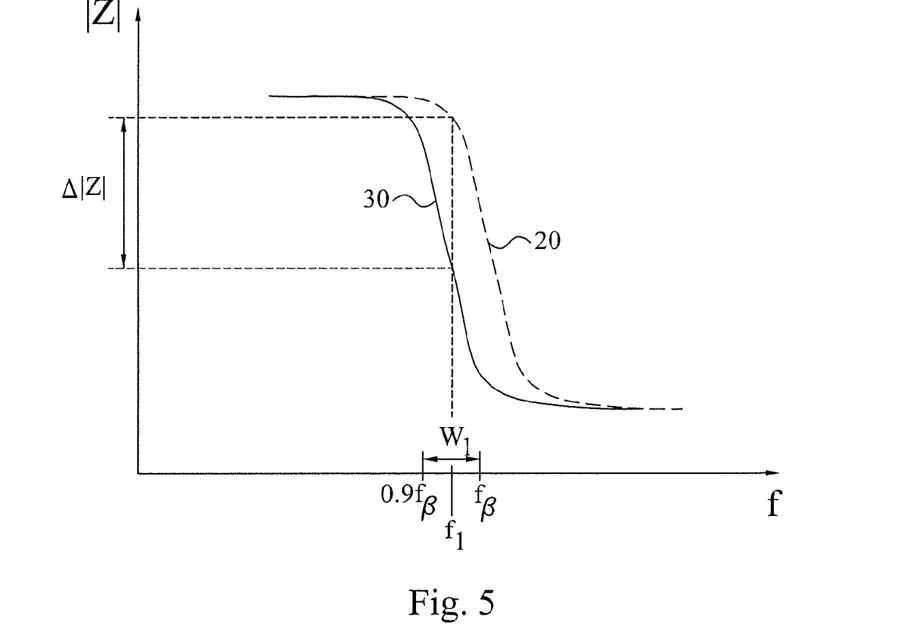
FIGS. 5 and 6 are diagrams schematically illustrating a difference a shift in impedance signal due to a change in permeability status of cell membranes in a tissue.

FIG. 5 is a graphical representation of the concept of utilizing the impedance parameter and reference parameter of the invention for the purpose of cell permeability monitoring. The figure illustrates the change in impedance (absolute value of complex impedance) over frequency. The hatched line 20 represents the impedance curve as measured for a healthy tissue. At low frequencies, i.e. $f \ll f_\beta$, where $f_\beta$ is the β-dispersion frequency, the current cannot pass through the cell membrane, thereby being limited to a current path around cells in the tissue. As the frequency nears $f_\beta$ the current starts to pass over the cell membranes, which starts to act more like a short circuit, thereby lowering the total impedance. At frequencies $f > f_\beta$ the current can pass through the cell membrane and the total impedance is rather unchanged until further dispersion events involving mitochondrial membranes at even higher frequencies.

The impedance measurements of the present invention are conducted in a frequency window W extending from $0.9 \times f_\beta$ to $f_\beta$. Thus, the signal generator generates a current or voltage signal at frequency $f_1$ present within this window W. The reference parameter can then be the absolute value of the impedance as determined at this frequency $f_1$ for the healthy tissue. At a later monitoring time, an ischemic event is taking place in the tissue, leading to increased intracellular edema. This basically corresponds to going from healthy cells as illustrated in the upper drawing of FIG. 1 to the more permeable cells of the lower drawing in FIG. 1. This effect causes a shift in the impedance curve from the curve 20 to the curve 30. If a current or voltage signal having the previous frequency $f_1$ in the window W is applied over the ischemic tissue, the resulting impedance parameter will be considerable lower than the previously determined reference parameter. The permeability status monitor and permeability detection can then be made based on the two parameters or a condition parameter, such as $\Delta |Z|$ calculated therefrom.

This latter embodiment is further illustrated in FIG. 4 which shows a possible implementation of the status monitor 150 of FIG. 2. The monitor 150 comprises a calculator 152 for calculating a condition parameter based on the impedance parameter and the reference parameter. This condition parameter could be a difference of the two parameters or a quotient of the parameters. A detector 154 is arranged in the monitor 150 for detecting a condition resulting in changes, preferably increased, cell permeability based on the condition parameter. Thus, such a condition is detected if the condition parameter falls outside of a pre-defined parameter interval corresponding to normal, healthy permeability status. For instance, if the condition parameter is the difference between the two parameters, $\Delta |Z| = |Z|_1 - |Z|_{ref}$, a membrane permeable condition is detected if $\Delta |Z| < T_1$, where $T_1$ is a defined threshold. Correspondingly, if the condition parameter is defined as $$\frac{|Z|_1}{|Z|_{ref}},$$

an increased cell permeability is detected if $$\frac{|Z|_1}{|Z|_{ref}} < T_2,$$

where $T_2$ is a threshold.

The permeability status monitoring of the present invention can be based on a single signal frequency present in the frequency window slightly below the β-dispersion frequency. In an alternative embodiment at least two signal frequencies present in different frequencies windows are employed by the IMD 100. In such a case, the signal generator 120 generates a first current or voltage signal at a first frequency present in a first frequency window from about 90% of the β-dispersion frequency to about the β-dispersion frequency for the tissue cell. The generator 120 also generates a second current or voltage signal at a second frequency present in a second frequency window from about the β-dispersion frequency to about 110% of the β-dispersion frequency. Thus, the first window is slightly less than the β-dispersion frequency, while the second window is slightly above the β-dispersion frequency. For instance, the second interval is preferably from about 101% to about 110% of the β-dispersion frequency.

The two current or voltage signals are applied in parallel or in series (at different time instances) to the tissue using the connected electrodes 210, 220, 230. The electrodes 210, 220, 230 capture a first resulting voltage or current signal and a second resulting voltage or current signal. The parameter determiner 140 calculates a first impedance parameter based on the first current/voltage signal and the first resulting voltage/current signal and determines a second impedance parameter based on the second current/voltage signal and the second resulting voltage/current signal. The monitor 150 uses both determined impedance parameters in the permeability status monitoring of the cells in the tissue.

The status monitor 150 preferably comprises a calculator 152, see FIG. 4, for calculating a difference between the first and second impedance parameter. The monitor 150 then monitors the permeability status and detects any abnormalities based on a comparison of the difference and a reference difference. This reference difference is preferably calculated from a previously determined first and second impedance parameter determined at a previous instant by the IMD 100.

Figure 6:
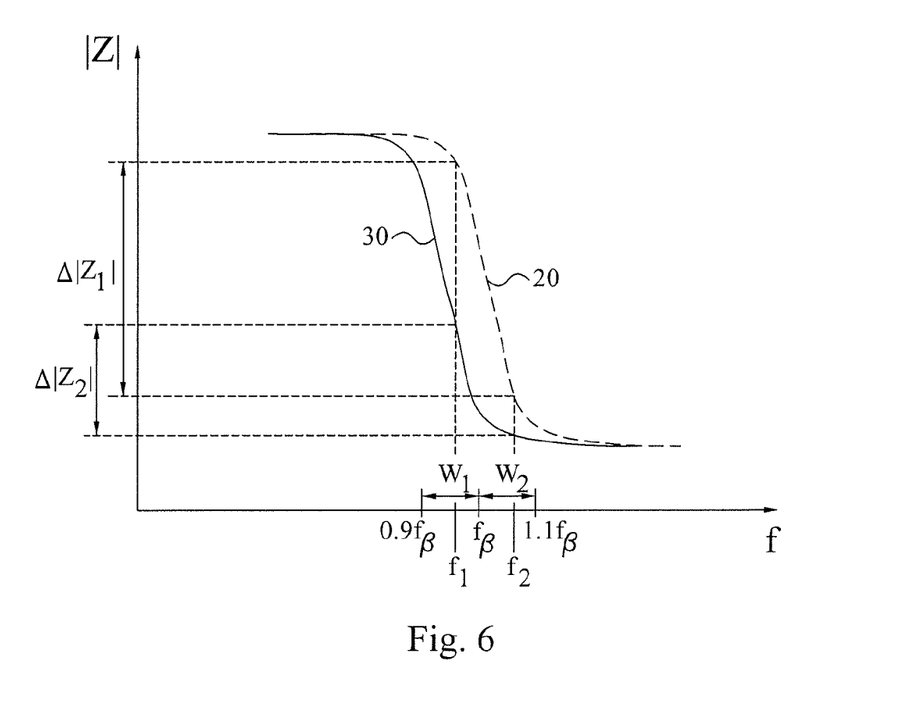

FIG. 6 illustrates the change in impedance at different frequencies for a healthy tissue, curve 20, and a tissue with abnormally high cell permeability, curve 30. The figure illustrates the two frequency windows, $W_1$, $W_2$, extending from $0.9 \times f_\beta$ to $f_\beta$ for window $W_1$ and from $f_\beta$ to $1.1 \times f_\beta$ for window $W_2$. The first current or voltage signal has a frequency $f_1$ present in the first window $W_1$, while the second signal has a frequency $f_2$ in the second window $W_2$. The difference $\Delta|Z_1|$ between the absolute impedance values (impedance parameter) at these two frequencies $f_1$, $f_2$ is calculated and stored in the IMD as reference parameter. Repeating the measurements during a membrane permeable condition (curve 20) at the same frequencies $f_1$, $f_2$ a new difference $\Delta|Z_2|$ between the impedance parameters is obtained. As is seen in the figure, in this case the new parameter difference is significantly smaller than the reference difference.

In similarity to above, the calculator 152 of the status monitor in FIG. 4 can calculate a condition parameter based on the difference $\Delta|Z_2|$ and the reference difference $\Delta|Z_1|$, such as a difference or quotient of the two differences. The detector 154 detects any condition resulting in abnormal, preferably increased, cell permeability based on the condition parameter, preferably by checking whether the condition parameter is within or is not present within a pre-defined parameter interval.

The interesting frequency, i.e. β-dispersion frequency that defines the one or two operational frequencies ($f_1$, $f_2$) of the applied current or voltage signal(s) could be hard-coded into the IMD 100, such as present in the memory 155. This means that information of that β-dispersion frequency or the operation frequency(ies) to use can be present in the memory 155 before implanting the IMD 100 in an animal body, preferably mammalian body and more preferably human body. In an alternative approach information of the β-dispersion frequency and/or operation frequency can be downloaded to the IMD 100 after implantation. In such a case, the IMD 100 has a receiver 190 with connected reception antenna 195. The information is preferably wirelessly transmitted as a message from an external or even remote RF transmitter. An optional message engine 180 is provided in the IMD 100 for extracting the desired frequency information and entering it in the memory 155 or directly providing it to the signal generator 120. In this approach it is actually possible to adjust the β-dispersion frequency and/or operational frequency(ies) over time if needed.

The above described embodiment of using pre-defined β-dispersion frequencies works well as the β-dispersion frequency is fairly similar for many cells, in particular regarding cells of a same or similar type and present in a same tissue, such as myocardial cells of a subject's heart.

In a more refined embodiment, the IMD 100 conducts a search procedure or algorithm for the purpose of identifying the β-dispersion frequency of a tissue to monitor. This procedure can be conducted following implantation of the IMD 100 in a subject body to get a starting β-dispersion frequency to use for identifying the frequency window of the applied current/voltage signal. The procedure can also be performed regularly or intermittently following implantation to detect any changes in β-dispersion frequency due to cell changes and/or changes to or in connection with the applying and sensing electrodes 210, 220, 230.

In this procedure, the signal generator 120 generates multiple current/voltage signals at multiple different frequencies, such as from a starting frequency $f_0$ and following frequencies $f_0 \pm k \times \Delta f$, where k=1, 2, 3, . . . N, N is a positive integer number, $\Delta f$ is a frequency hop. It is though anticipated by the present invention that the multiple current/voltage signals must not necessarily be of uniformly increasing or decreasing frequencies. The signals are applied to the tissue using the electrodes 210, 220, 230 and the multiple resulting voltage or current signals are measured by the signal measurer 130. The parameter determiner 140 calculates, from respective signal pairs of the applied and measured signals, multiple impedance parameters representative of the impedance of the tissue at the different frequencies. A frequency identifier 170 is provided in the IMD 100 for processing the determined impedance parameters for the purpose of identifying the current β-dispersion frequency of the tissue.

This frequency identifier 170 could for instance calculate pairwise differences between two impedance parameters corresponding to neighboring frequencies in the frequency sweep. When going from lower towards higher frequencies, the pairwise difference increases as one approaches the β-dispersion frequency and then decrease passing the β-dispersion frequency. This means that the frequency used for impedance parameter having the largest associated pairwise difference or at least such a difference exceeding a threshold is selected as the β-dispersion frequency of the tissue.

An alternative but somewhat related embodiment would be to determine the first derivate of the impedance parameter with regard to frequency. In such a case, the β-dispersion frequency corresponds to a maximum, typically global maximum, in the tested frequency interval.

Once the β-dispersion frequency has been identified by the frequency identifier 170, information thereof can be provided to the memory 155 for storage or to the signal generator 120. In either case, the signal generator 120 is programmed to apply current/voltage signals for the permeability monitoring having a frequency present in the first or second frequency interval that precedes or follows the β-dispersion frequency.

This embodiment of providing a frequency sweeping functionality relaxes the need for any hard-coding or external communication of pre-defined β-dispersion frequencies. In clear contrast, a starting β-dispersion frequency that is determined for the particular tissue and for the given IMD and electrode arrangement is instead used, giving a much more accurate monitored frequency window.

The IMD 100 of the present invention can be used for monitoring and detecting different conditions affecting the permeability of the cells in a tissue. A typical such condition is the anoxic condition preceding tissue ischemia, which causes intracellular edema and cell swelling. There are though many other sources and conditions that give rise to cell permeability changes and that can be monitored and detected according to the present invention. For instance, it has been shown that radiation, such as X-ray radiation, and heavy metal salts both apart and together affects the permeability of cell membranes (*Radiats Biol Radioecol*, 47(1): 117-124, 2007) A hypotonic shock also alters the cell permeability (*FEBS Lett*, 276(1-2): 6-8, 1990) as does cardiac dysfunction in cardiomyopathies (*Am J Physiol Heart Circ Physiol*, 278 (4): H1362-H1370, 2000). Crohn's disease may cause significant changes in the permeability of the cell membrane (*European Journal of Nuclear Medicine and Molecular Imaging*, 8(6): 245-249, 1983) as do many inherited hemolytic anemias, such as hereditary spherocytosis, hereditary elliptocytosis, hereditary pyropoikilocytos and hereditary stomatocytosis (*American Society of Hematology*, 1: 13-18, 2005). Furthermore, apoptosis causes the cell membrane to collapse, thereby altering the structure of the cell membranes and their permeability. The present invention can therefore be used for monitoring and detecting medical conditions leading to apoptosis of cells in a tissue.

In a preferred embodiment of the invention, the present invention is used for monitoring permeability changes of cell membranes in cardiogenic tissue, such as in the myocardium. In such a case, the IMD 100 may comprise an IEGM determiner 160 arranged for recording an intracardiac electrogram (IEGM) based on electrical signals of the heart tissue sensed by at least one of the electrodes 210, 220, 230 connected to the IMD 100. This IEGM recording can be made conditional upon detection of a permeability-effecting condition by the status monitor 150. Thus, if the monitor 150 detects, based on the determined impedance parameter(s), a significant change in the membrane permeability of the heart tissue, it controls the IEGM determiner 160 to record an IEGM over one or more heart cycles. The recorded IEGM data is, in connection with the impedance data, of highly diagnostic value and is therefore preferably entered in the memory 155 for later retrieval, such as during a follow-up visit at a healthcare facility. In addition, or alternatively, the message engine 180 can compose a data message comprising the IEGM data and impedance data of the invention. The composed message is forwarded to a transmitter 190 having a connected transmitting antenna 195. The message can then be wirelessly transmitted to an external communications unit, such as the programmer of FIG. 2 or a PDA assigned to the subject.

The units 120 to 190 of the IMD 100 can be implemented in hardware, software of a combination of hardware and software.

Figure 7:
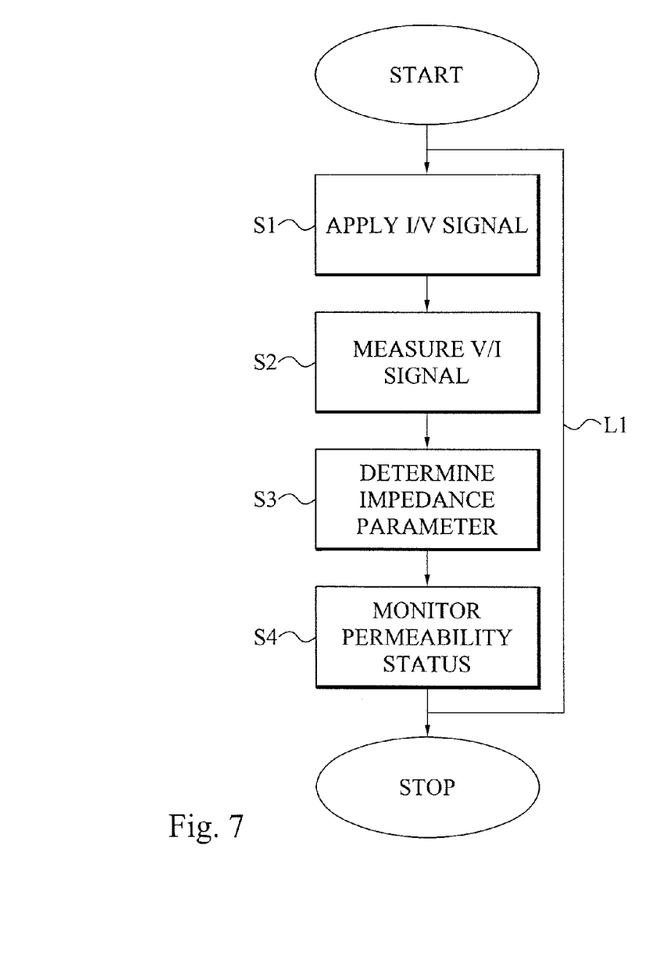
FIG. 7 is a flow diagram of a method of a status monitoring method according to an embodiment of the present invention.

FIG. 7 is a flow diagram of a method of monitoring permeability status of cell membranes in a tissue of a subject. The method starts in step S1, where a current or voltage signal of selected frequency is generated by a signal source arranged in an IMD and applied to a tissue in an animal, preferably mammalian and more preferably human body utilizing two electrodes connected to the IMD, such as provided on one or two leads connected to the IMD. The generated and applied current/voltage signal has a frequency present in a frequency window extending from about 90% of the β-dispersion frequency for the tissue to about the β-dispersion frequency.

A resulting voltage/current signal is sensed by two electrodes in step S2, where the electrodes can be the same or different from the signal applying electrodes. Step S3 uses the measured voltage/current signal together with the applied current/voltage signal or information of the applied current/voltage signal (such as frequency, amplitude, phase) for determining an impedance parameter, such as complex impedance parameter, impedance amplitude, phase angle, etc. This impedance parameter is processed in step S4 and employed for monitoring the permeability status of cell membranes in the tissue.

The monitoring method of steps S1 to S4 is preferably performed at multiple different time instances, such as intermittently or periodically, which is schematically illustrated by the line L1. The method then ends.

Figure 8:
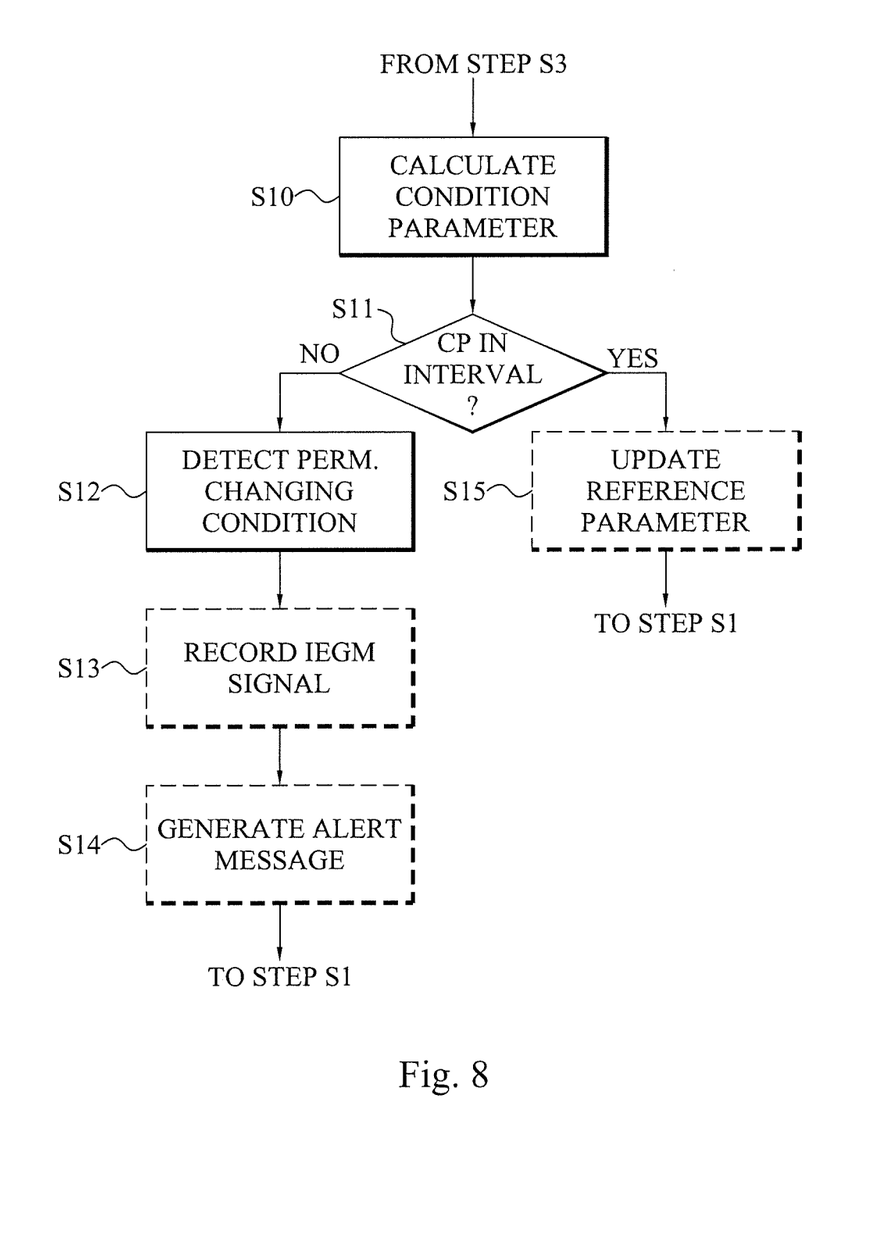
FIG. 8 is a flow diagram of an embodiment of the monitoring step S4 of the status monitoring method in FIG. 7.

FIG. 8 is a flow diagram illustrating an embodiment of the monitoring step S4 of FIG. 7. The method continues from step S3 of FIG. 7. A next step S10 calculates a condition parameter based on the determined impedance parameter and a reference parameter, such as determined based on one or more previously conducted impedance measurements for the tissue. The condition parameter, CP, could, for instance, be a difference, the absolute value of the difference between or the quotient of the impedance parameter and the reference parameter. The next step S11 investigates whether the condition parameter is present within an interval corresponding to no significant permeability changes. If the parameter is within the interval, the method continues to the optional step S15, where the reference parameter is updated based on the determined impedance parameter. A new updated reference parameter is calculated, preferably as an average, possibly weighted average, of the impedance parameter and the previous reference parameter. The method then continues to step S1 of FIG. 7.

However, if the condition parameter exceeds the normal interval, a permeability change of the tissue cell membranes has occurred. The next step S12 therefore detects a condition resulting in a permeability changing, typically increasing condition in the tissue. If the monitored tissue is a heart tissue, the condition detection optionally triggers the recording of an IEGM signal from the heart tissue in step S13. An alert message can be generated in step S14 comprising information of the detected permeability changing condition, preferably including the determined impedance parameter and/or condition parameter and preferably also the recorded IEGM data. The message is either stored in the IMD for later retrieval or wirelessly sent to an external unit. The method then continues to step S1 of FIG. 7.

As was described in the foregoing, a second current or voltage signal having a frequency in a window slightly above the β-dispersion frequency of the tissue, such as from about the β-dispersion frequency to about 110% of the β-dispersion frequency, is applied over the tissue. A resulting second voltage or current signal is measured and a second impedance parameter representative of the impedance of the tissue is determined based on the second current/voltage signal and the second resulting voltage/current signal is determined. The permeability status monitoring is then made based on the first and second impedance parameter.

The monitoring preferably involves calculating a difference between the two impedance parameters and comparing this difference to a reference difference previously calculated from at least one previous first impedance parameter (frequency in window $W_1$) and at least one previous second impedance parameter (frequency in window $W_2$). For instance, a condition parameter can be calculated from the difference and the reference difference and used in the monitoring and detection of the invention as previously described.

Figure 9:
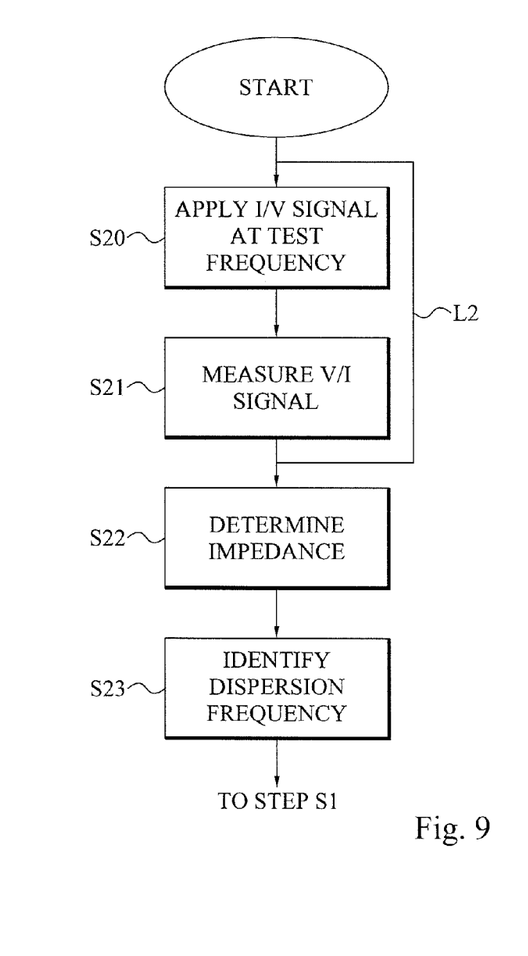
FIG. 9 is a flow diagram illustrating additional steps of the status monitoring method in FIG. 7.

FIG. 9 is a flow diagram illustrating additional steps of the monitoring method, which involve performing a frequency sweep for the purpose of identifying the β-dispersion frequency of the tissue cells. The method starts in step S20 where a current or voltage signal is applied at a first test frequency over at least a portion of the tissue. The resulting voltage or current signal is then measured in step S21. The loop of steps S20 and S21 are repeated multiple times, schematically illustrated by the line L2, but with different test frequencies to thereby obtain a frequency spectrum of impedance signals determined in step S22 for the different signals. This impedance spectrum consisting of impedance parameters at the different test frequencies is processed in step S23 for the purpose of identifying the β-dispersion frequency of the tissue. Any of the previously described embodiments can be employed in this frequency identification. The method then continues to step S1 of FIG. 7.

It will be understood by those skilled in the art that various modifications and changes may be made to the present invention without departure from the scope thereof, which is defined by the appended claims.

We claim as our invention:

1. An implantable medical device comprising:
   at least two implantable electrodes configured to communicate electric signals with a tissue;
   a memory configured to store a predetermined value representative of a β-dispersion frequency associated with cell membranes in said tissue;
   a signal generator configured to generate a first signal at a frequency in a first frequency window as a function of the stored predetermined value representative of the β-dispersion frequency, the frequency window extending from the stored predetermine value representative of the β-dispersion frequency to a frequency corresponding to about 90% of the stored value representative of said β-dispersion frequency, said first signal being communicated to said tissue via said at least two implantable electrodes;
   a signal measurer configured to measure a first resulting signal collected by said at least two implantable electrodes;
   a parameter determiner configured to determine, based on said first signal and said first resulting signal, a first impedance parameter representative of an impedance of said tissue; and
   a status monitor configured to monitor a permeability status of said cell membranes in said tissue based on said first impedance parameter.

2. The device according to claim 1, wherein said signal generator generates said first signal at a frequency in a first frequency window extending from a frequency corresponding to about 99% of said β-dispersion frequency to said frequency corresponding to about 90% of said β-dispersion frequency.

3. The device according to claim 1, wherein said status monitor monitors said permeability status based on a comparison of said first impedance parameter and a reference impedance parameter.

4. The device according to claim 3, wherein said reference impedance parameter is a previously determined impedance parameter representative of an impedance of said tissue at a previous time instance.

5. The device according to claim 3, wherein said status monitor comprises:
   a calculator configured to calculate a condition parameter based on said first impedance parameter and said reference impedance parameter; and
   a detector configured to detect a condition resulting in an increase in cell permeability if said condition parameter is not present within a pre-defined parameter interval.

6. The device according to claim 1, wherein said signal generator is further configured to generate a second signal at a frequency in a second frequency window extending from said β-dispersion frequency to a frequency corresponding to about 110% of said β-dispersion frequency, said second signal being communicated to said tissue via said at least two implantable electrodes, said signal measurer is further configured to measure a second resulting signal collected by said at least two electrodes, said parameter determiner is further configured to determine, based on said second signal and said second resulting signal, a second impedance parameter representative of an impedance of said tissue, and said status monitor configured to monitor said permeability status based on said first impedance parameter and said second impedance parameter.

7. The device according to claim 6, wherein said signal generator generates said second signal at a frequency in a second frequency window extending from a frequency corresponding to about 101% of said β-dispersion frequency to said frequency corresponding to about 110% of said β-dispersion frequency.

8. The device according to claim 6, further comprising a calculator configured to calculate a difference between said first impedance parameter and said second impedance parameter, and wherein said status monitor is configured to monitor said permeability status based on a comparison of said difference and a reference difference calculated between a first reference impedance parameter and a second reference impedance parameter.

9. The device according to claim 8, wherein said first reference impedance parameter is a previously determined impedance parameter representative of an impedance of said tissue at a previous time instance obtained by applying a signal at a frequency in said first frequency window and said second reference impedance parameter is a previously determined impedance parameter representative of an impedance of said tissue at a previous time instance obtained by applying a signal at a frequency in said second frequency window.

10. The device according to claim 8, wherein said status monitor comprises:
    a calculator configured to calculate a condition parameter based on said difference between said first impedance parameter and said second impedance parameter and said difference between said first reference impedance parameter and said second reference impedance parameter; and
    a detector configured to detect a condition resulting in an increase in cell permeability if said condition parameter is not present within a pre-defined parameter interval.

11. The device according to claim 10, wherein said condition is intracellular edema.

12. The device according to claim 10, wherein said tissue is a heart tissue and said implantable medical device further comprising an intracardiac electrogram determiner that records, upon detection of said condition, an intracardiac electrogram based on electrical signals of said heart tissue sensed by at least one electrode of said at least two electrodes.

13. The device according to claim 1, wherein said signal generator generates signals at multiple different frequencies, said signals being applicable using said at least two implantable electrodes, and wherein said signal measurer measures resulting signals collected by said at least two implantable electrodes, and wherein said parameter determiner determines, based on respective pairs of said signals and said resulting signals, impedance parameters representative of the impedance of said tissue at different frequencies, and wherein said implantable medical device comprises a frequency identifier configured to identify said β-dispersion frequency based on said impedance parameters.

14. The device according to claim 13, wherein said frequency identifier identifies said p-dispersion frequency as a frequency at which a difference between the impedance parameter at a first frequency and the impedance parameter at a next frequency of said multiple frequencies exceeds a threshold.

15. A method of monitoring permeability status of cell membranes in a tissue comprising the steps of:

storing a predetermined value representative of a p-dispersion frequency in a memory, wherein the β-dispersion frequency is associated with said cell membranes in said tissue;

applying a first signal over at least a portion of said tissue at a frequency in a first frequency window as a function of the stored predetermined value representative of the β-dispersion frequency, the frequency window extending from the stored predetermined value representative of the β-dispersion frequency of said cell membranes to a frequency corresponding to about 90% of said β-dispersion frequency;

measuring a first resulting signal;

determining, based on said first signal and said first resulting signal, a first impedance parameter representative of an impedance of said tissue; and monitoring a permeability status of cell membranes in said tissue based on said first impedance parameter.

16. The method according to claim 15, wherein said monitoring step comprises monitoring said permeability status based on a comparison of said first impedance parameter and a previously determined impedance parameter representative of an impedance of said tissue at a previous time instance.

17. The method according to claim 16, wherein said monitoring step comprises the steps of:
calculating a condition parameter based on said first impedance parameter and said previously determined impedance parameter; and
detecting a condition resulting in an increase in cell permeability if said condition parameter is not present within a pre-defined parameter interval.

18. The method according to claim 15, further comprising the steps of:
applying a second signal over said at least a portion of said tissue at a frequency in a second frequency window extending from said β-dispersion frequency to a frequency corresponding to about 110% of said β-dispersion frequency;
measuring a second resulting signal; and
determining, based on said second signal and said second resulting, a second impedance parameter representative of an impedance of said tissue, wherein said monitoring step comprises monitoring said permeability status based on said first impedance parameter and said second impedance parameter.

19. The method according to claim 18, wherein said monitoring step comprises the steps of:
calculating a difference between said first impedance parameter and said second impedance parameter; and
monitoring said permeability status based on a comparison of said difference and a reference difference calculated between a first reference impedance parameter and a second reference impedance parameter.

20. The method according to claim 19, wherein said monitoring step comprises the steps of:
calculating a condition parameter based on said difference between said first impedance parameter and said second impedance parameter and said difference between said first reference impedance parameter and said second reference impedance parameter; and
detecting a condition resulting in an increase in cell permeability if said condition parameter is not present within a pre-defined parameter interval.

21. The method according to claim 17, wherein said tissue is heart tissue and said method further comprising recording an intracardiac electrogram upon detection of said condition.

22. The method according to claim 15, further comprising the steps of:
applying signals over at least a portion of said tissue at multiple different frequencies;
measuring resulting signals;
determining, based on respective pairs of said signals and said resulting signals, impedance parameters representative of the impedance of said tissue at different frequencies; and
identifying said β-dispersion frequency based on said impedance parameters.

23. The device according to claim 1, wherein said first resulting signal is a current signal when said first signal is a voltage, and said first resulting signal is a voltage signal when said first signal is a current signal.

24. The method according to claim 15, wherein said first resulting signal is a current signal when said first signal is a voltage signal, and said first resulting signal is a voltage signal when said first signal is a current signal.

* * * * *